(12) United States Patent
Blasco et al.

(10) Patent No.: US 8,399,056 B2
(45) Date of Patent: *Mar. 19, 2013

(54) METHOD OF FORMING HIGH-K DIELECTRIC FILMS BASED ON NOVEL TITANIUM, ZIRCONIUM, AND HAFNIUM PRECURSORS AND THEIR USE FOR SEMICONDUCTOR MANUFACTURING

(75) Inventors: Nicolas Blasco, Grenoble (FR); Christian Dussarrat, Wilmington, DE (US)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 793 days.

This patent is subject to a terminal disclaimer.

(21) Appl. No.: 12/303,165

(22) PCT Filed: Jun. 2, 2006

(86) PCT No.: PCT/EP2006/062893
§ 371 (c)(1),
(2), (4) Date: Aug. 14, 2009

(87) PCT Pub. No.: WO2007/140813
PCT Pub. Date: Dec. 13, 2007

(65) Prior Publication Data
US 2009/0311879 A1    Dec. 17, 2009

(51) Int. Cl.
*C23C 16/40* (2006.01)
(52) U.S. Cl. ......... 427/255.31; 427/255.33; 427/255.34; 427/255.35; 427/255.36; 427/255.394
(58) Field of Classification Search ............ 427/255.31, 427/355.36, 255.394, 255.33, 255.34, 255.35, 427/255.26; 117/84
See application file for complete search history.

(56) References Cited

U.S. PATENT DOCUMENTS

| | | | |
|---|---|---|---|
| 5,527,752 A | 6/1996 | Reichle et al. | |
| 5,861,352 A | 1/1999 | Gila et al. | |
| 5,970,604 A | 10/1999 | Person et al. | |
| 6,001,742 A | 12/1999 | Chang | |
| 6,197,683 B1 | 3/2001 | Kang et al. | |
| 6,689,675 B1 * | 2/2004 | Parker et al. | 438/585 |
| 6,743,473 B1 | 6/2004 | Parkhe et al. | |
| 6,858,547 B2 | 2/2005 | Metzner et al. | |
| 6,984,591 B1 | 1/2006 | Buchanan et al. | |
| 7,108,747 B1 | 9/2006 | Leskela et al. | |
| 7,157,780 B2 * | 1/2007 | Harada | 257/410 |
| 7,833,913 B2 * | 11/2010 | Clark | 438/785 |
| 2001/0001949 A1 | 5/2001 | Westmoreland et al. | |
| 2002/0042165 A1 | 4/2002 | Putkonen | |
| 2004/0198069 A1 * | 10/2004 | Metzner et al. | 438/785 |
| 2004/0235312 A1 | 11/2004 | Loftin et al. | |
| 2005/0260357 A1 * | 11/2005 | Olsen et al. | 427/569 |
| 2006/0062910 A1 | 3/2006 | Meiere | |
| 2006/0062917 A1 * | 3/2006 | Muthukrishnan et al. | 427/248.1 |
| 2006/0097305 A1 | 5/2006 | Lee | |
| 2005/0056219 A1 | 8/2006 | Song et al. | |
| 2006/0228888 A1 | 10/2006 | Lee et al. | |
| 2007/0001231 A1 * | 1/2007 | Currie | 257/368 |
| 2009/0203222 A1 * | 8/2009 | Dussarrat et al. | 438/778 |
| 2011/0207337 A1 * | 8/2011 | Dussarrat et al. | 438/785 |

FOREIGN PATENT DOCUMENTS

| | | |
|---|---|---|
| EP | 0 808 841 | 11/1997 |
| EP | 1 067 595 | 1/2001 |
| EP | 1 524 299 | 4/2005 |
| JP | 10 503242 | 3/1998 |
| JP | 32 30805 | 11/1999 |
| JP | 2001 102326 | 4/2001 |
| JP | 2001 355070 | 12/2001 |
| JP | 2002 060944 | 2/2002 |
| JP | 2002 069641 | 3/2002 |
| JP | 2002 093803 | 3/2002 |
| JP | 2002 525426 | 8/2002 |
| JP | 2004 507551 | 3/2004 |
| JP | 2004 300579 | 10/2004 |
| JP | 2004 349710 | 12/2004 |
| JP | 2005 104994 | 4/2005 |
| JP | 2005 171291 | 6/2005 |
| JP | 2005 209766 | 8/2005 |
| JP | 2005 536064 | 11/2005 |
| JP | 2005 351450 | 12/2005 |
| JP | 2011 071628 | 4/2011 |
| WO | WO 96 27032 | 9/1996 |
| WO | WO 02 18394 | 3/2002 |
| WO | WO 03 035926 | 5/2003 |
| WO | WO 2004 010469 | 1/2004 |
| WO | WO 2005 113852 | 12/2005 |
| WO | WO 2007 140813 | 6/2006 |
| WO | WO 2007 141059 | 6/2006 |
| WO | WO 2006 131751 | 12/2006 |
| WO | WO 2007 005088 | 1/2007 |
| WO | WO 2007 011973 | 1/2007 |
| WO | WO 2007 030673 | 3/2007 |
| WO | WO 2007 066546 | 6/2007 |

OTHER PUBLICATIONS

Becker, Jill S., et al., "Atomic Layer Deposition of Insulating Hafnium and Zirconium Nitrides". Chem. Mater. 2004, 16, 3497-3501.*

Zhu, J., et al., "Enhanced dielectric properties of ZrO2 thin films prepared in nitrogen ambient by pulsed laser deposition." J. Phys. D: Appl. Phys. 36 (2003) pp. 389-393.*

Pezzi, R.P., et al., "Hydrogen and deuterium incorporation and transport in hafnium-based dielectric films on silicon". Applied Physics Letters, vol. 85, No. 16, Oct. 18, 2004, pp. 3540-3542.*

(Continued)

*Primary Examiner* — Bret Chen
(74) *Attorney, Agent, or Firm* — Patricia E. McQueeney

(57) ABSTRACT

A method of forming on at least one support at least one metal containing dielectric films having the formula $(M^1_{1-a} M^2_a) O_b N_c$, wherein: $0 \leq a < 1$, 01 and $M^2$ being metals Hf, Zr or Ti using precursors with pentadienyl ligands and/or cyclopentadienyl ligands.

16 Claims, No Drawings

OTHER PUBLICATIONS

Chen, P., et al., "Effect of nitrogen containing plasmas on interface stability of hafnium oxide ultrathin films on Si(100)". Applied Physics Letters, vol. 85, No. 9, Aug. 30, 2004, pp. 1574-1576.*

Codato, Simone, et al., "MOCVD Growth and Characterization of ZrO2 Thin Films Obtained from Unusual Organo-Zirconium Precursors." Chemical Vapor Deposition 1999, 5, No. 4, pp. 159-164.*

Carta, G. et al., "Thermal properties of volatile organohafnium precursors for $HfO_2$ MOCVD processes," Electrochemical Society Proceedings vol. 2005-09, pp. 260-267.

Caymax, M. et al., "High-k materials for advanced gate stack dielectrics: a comparison of ALCVD and MOCVD as deposition technologies," 2003 Materials Research Society Symposium Proceedings, vol. 765, pp. 47-58.

Chandra et al., "Amido-derivatives of metals and metalloids. Part VI. Reactions of titanium(IV), zirconium(IV), and hafnium(IV) amides with protic compounds," J. Chem. Soc. (A), 1968, pp. 1940-1945.

Cotton, S.I., "Ti, Zr, and Hf," Annu. Rep. Prog. Chem. Sect. A: Inorg. Chem 1993, 90, pp. 119-130.

Kim, M-S et al., "ALD analyses of HfCl4+O3 and HfCl4+H2O by mass spectroscopy," Electrochemical Society Proceedings vol. 2005-05, pp. 397-403.

Kukli, K. et al., "Atomic layer deposition of hafnium dioxide films from 1-methoxy-2-methyl-2-propanolate complex of hafnium," Chem Mater. 2003, 15, pp. 1722-1727.

Lehn, J-S et al., "New precursors for the DVD of zirconium and hafnium oxide films," Chem Vap. Deposition 2006, 12, pp. 280-284.

Potter, R.J. et al., "Deposition of $HfO_2$, $Gd_2O_3$ and $PrO_x$ by liquid injection ALD techniques," Chem. Vap. Deposition 2005, 11, No. 3, pp. 159-169.

Ritala, M. et al., "Atomic Layer Deposition," Ch.2, Handbook of Thin Film Materials, H.S. Nalwa, ed., vol. 1, "Deposition and Processing of Thin Films," Academic Press, San Diego, CA, 2002.

Williams, P.A. et al., "Novel mononuclear alkoxide precursors for the MOCVD of ZrO2 and HfO2 thin films," Chem Vap. Deposition 2002, 8, No. 4, pp. 163-170.

Written Opinion for co-pending PCT/EP2006/062893, Sep. 27, 2007.

International Search Report and Written Opinion for related PCT/EP2006/052507, Oct. 31, 2007.

International Search Report and Written Opinion for related PCT/EP2009/051683, May 14, 2009.

Triyoso, D.H. et al. "Physical and electrical characteristics of $HfO_2$ gate dielectrics deposited by ALD and MOCVD." J. Electrochem. Soc., 152 (3) G203-G209 (2005).

Chang, H.S. et al. "Electrical and physical properties of HfO2 deposited via ALD using $Hf(OtBu)_4$ and ozone atop $Al_2O_3$." Electrochem. Solid-State Letters, 7 (6) F42-F44 (2004).

Senzaki, Y. et al. "Atomic layer deposition of hafnium oxide and hafnium solicate thin films using liquid precursors and ozone." J. Vac. Sci. Technol. A 22(4), Jul./Aug. 2004.

Hausmann, D.M. et al. "Atomic layer deposition of hafnium and zirconium oxide using metal amide precursors." Chem., Mater. 2002, 14, 4350-4353.

Kawahara, T. et al. "Effect of Hf source, oxidizing agents, and $NH_3$/Ar plasma on the properties of $HfAlO_x$ films prepared by atomic layer deposition." J. Appl. Phys., vol. 43, No. 7A, 2004, pp. 4129-4134.

Putkonen, M. et al. "Zirconia thin films by atomic layer epitaxy. A comparative study on the use of novel precursors with ozone." J. Mater. Chem., 3141, 11, 2001.

Niinisto, J. et al. "In situ quadrupole mass spectrometry study of atomic-layer deposition of $ZrO_2$ using $Cp_2Zr(CH_3)_2$ and water." Langmuir, 7321, 21, 2005.

Juppo, M. et al. "In situ mass spectrometry study on surface reactions in atomic layer deposition of $Al_2O_3$ thin films from trimethylaluminum and water." Langmuir 2000, 16, pp. 4034-4039.

Patent Abstracts of Japan, publication No. 2002093804, publication date Mar. 29, 2002, application No. 2000282198, application date Sep. 18, 2000.

International Search Report for PCT/EP2006/062893.

Codato S., et al. "MOCVD growth and characterization of $ZrO_2$ thin films obtained from unusual organo-zirconium precursors." Chemical Vapor Deposition, Wiley-VCH Verlag, Weinheim, Germany, vol. 11, No. 11, 1999, pp. 159-164.

Becker, J.S. et al., "Atomic layer deposition of insulating hafnium and zirconium nitrides," Chem. Mater. 2004, 16, pp. 3497-3501.

Cano, J. et al., "Neutral and Cationic [bis($\eta^1$-amidosilyl)-$\eta^5$-cyclopentadienyl]titanium and -zirconium complexes: synthesis, x-ray molecular structures and DFT calculations," Eur. J. Inorg. Chem. 2003, p. 2463-2474.

Chen, P. et al., "Effect of nitrogen containing plasmas on interface stability of hafnium oxide ultrathin films on Si(100)," Applied Physics Letters, Aug. 30, 2004, vol. 85, No. 9, pp. 1574-1576.

Ciruelo, G. et al., "Synthesis and reactivity of new silyl substituted monocyclopentadienyl zirconium complexes. X-ray molecular structure of $[Zr\{\eta^5\text{-}C_5H_4(SiMe_2CH_2Ph)\}(CH_2Ph)_3]$," Journal of Organometallic Chemistry, 547 (1997), pp. 287-296.

Irigoyen, A.M. et al., "Synthesis and characterisation of chlorobis(dialkylamindo) and alkylbis(dialkylamido) derivatives of $[(\eta^5\text{-}C_5Me_5)MCl_3](M=Ti,Zr)$," Journal of Organometallic Chemistry 494 (1995), pp. 255-259.

Jutzi, P. et al., "Halfsandwich-Komplexe der Elemente Titan und Zirconium mit dem (Diisopropylaminoethyl) cyclopentadienyl-Ligand: Molekülstruktur von $[(C_5H_4CH_2CH_2N(H)^1Pr_2)ZrCl_3]^+Cl \cdot 2CH_3OH$," Journal of Organometallic Chemistry 533 (1997), pp. 237-245.

Rogers, J.S. et al., "Fulvene to cyclopentadienyl conversion with homoleptic complexes of zirconium and hafnium," Organometallics 1999, 18, pp. 3976-3980.

Schneider, H. et al., "Immobilization of η 5-cyclopentadienyltris(dimethylamido) zirconium polymerization catalysts on a chlorosilane- and JMDS-modified meosporous silica surface: a new concept for supporting metallocene amides towards heterogenous single-site-catalysts," Journal of Molecular Catalysis A: Chemical, 170 (2001), pp. 127-141.

Winter, C.H. et al., "Metallic materials deposition: metal-organic precursors," Encyclopedia of Inorganic Chemistry, 2006, published online Mar. 15, 2006, accessed at http://onlinelibrary.wiley.com/doi/10.1002/0470862106.ia.138/abstract, 25 pgs.

* cited by examiner

METHOD OF FORMING HIGH-K DIELECTRIC FILMS BASED ON NOVEL TITANIUM, ZIRCONIUM, AND HAFNIUM PRECURSORS AND THEIR USE FOR SEMICONDUCTOR MANUFACTURING

This application is a 371 of International PCT Application PCT/EP2006/062893, filed Jun. 2, 2006.

The invention relates to a method of forming high-k dielectric films such as hafnium or zirconium oxides or oxynitrides and their use for manufacturing semi-conductors.

BACKGROUND

With the shrink of the critical dimensions of the future generation of semi-conductor devices, the introduction of new materials, especially having high dielectric constant, is required. In CMOS architectures, high-k dielectrics are required to replace $SiO_2$ which reaches its physical limits, having typically a $SiO_2$ equivalent thickness of about 1 nm.

Similarly, high-k dielectrics are required in Metal-Insulator-Metal architectures for RAM applications. Various metal compositions have been considered to fulfill both the materials requirements (dielectric constant, leakage current, crystallisation temperature, charge trapping) and the integration requirements (thermal stability at the interface, dry etching feasibility . . . ).

The Group IV based materials, such as $HfO_2$, $HfSiO_4$, $ZrO_2$, $ZrSiO_4$, $HfZrO_4$, $HfLnO_x$ (Ln being selected from the group comprising scandium, yttrium and rare-earth elements) are among most promising materials. Furthermore, Group IV metals composition can also be considered for electrode and/or Cu diffusion barrier applications, such as TiN for mid-gap metal gate and MIM RAM, HfN, ZrN, HfSi, ZrSi, HfSiN, ZrSiN, TiSiN . . . .

Deposition processes of such thin films with reasonable throughput and acceptable purity are vapor phase deposition techniques, such as MOCVD (Metal-organic Chemical Vapor Deposition) or ALD (Atomic Layer Deposition). Such deposition processes require metal precursors that must fulfill drastic requirements for a proper industrial use.

It is known from Kim et al., Electrochem Soc Proceedings 2005-05, 397, 2005, to use $HfCl_4$ for the deposition of $HfO_2$ by ALD. However, some by-products generated during the deposition process, such as HCl or $Cl_2$, can cause surface/interface roughness that can be detrimental to the final properties. Other possible byproducts, depending on the oxygen source used, may be hazardous. For instance, $OCl_2$, through the OCl fragment by QMS, has been detected as a byproduct of the reaction between $HfCl_4$ and $O_3$. Moreover, in the case of high-k oxide, Cl or F impurities are detrimental to the final electrical properties and Cl and F-containing precursors are therefore not preferred.

Triyoso et al. in J. Electrochem. Soc. 152 (3) G203-G209 (2005), Chang et al. in Electrochem. Solid. State Let., 7 (6) F42-F44 (2004), studied the use of $Hf(OtBu)_4$ for $HfO_2$ MOCVD and ALD, respectively. Williams et al. have evaluated $Hf(mmp)_4$ and $Hf(OtBu)_2(mmp)_2$ for MOCVD of $HfO_2$. In WO2003035926, Jones et al. disclose solid Ti, Hf, Zr and La precursors improved with donor functionalized alkoxy ligand (1-methoxy-2-methyl-2-propanolate [$OCMe_2CH_2OMe$, mmp]) which helps inhibiting oligomerisation of Zr and Hf alkoxide compounds and increasing their stability towards moisture. However, all those alkoxide precursors have the drawback not to enable self-limited deposition in ALD process.

Alkylamides precursors such as $Hf(NEtMe)_4$, $Hf(NMe_2)_4$, $Hf(NEt_2)_4$ . . . have been widely disclosed in the literature such as by Senzaki et al in J. Vac. Sci. Technol. A 22(4) July/August 2004, Haussmann et al. in Chem. Mater. 2002, 14, 4350-4353, Kawahara et al. in J. Appl. Phys., Vol 43, No. 7A, 2004, pp 4129-4134, Hideaki et al. in JP2002093804, Metzner et al. in U.S. Pat. No. 6,858,547, Dip et al. in US20050056219. Group IV alkylamides are both suitable for ALD and MOCVD processes. Furthermore, some are liquid at room temperature (TDEAH and TEMAH) and of sufficient volatility, and they allow self-limited ALD at low temperature for a limited thermal budget process. However, Group IV alkylamides have several drawbacks:

they may decompose during the distribution to some extent leading to a possible clogging of the feeding line or the vaporizer, they may generate particles during deposition, they may entail non-uniform compositions during deep trenches deposition processes, they only allow a narrow self-limited ALD temperature window, hence reducing the process window.

Carta et al. disclose in Electrochem Soc Proceedings, 260, 2005-09, 2005 the use of bis(cyclopentadienyl)bisdimethyl hafnium and several authors (Codato et al., Chem Vapor Deposition, 159, 5, 1995; Putkonen et al., J Mater Chem, 3141, 11, 2001; Niinisto et al., Langmuir, 7321, 21, 2005) disclose the use of bis(cyclopentadienyl)bisdimethyl zirconium, which allow an efficient ALD deposition process with an ALD window up to 400° C. and an achievement of films with less than 0.2% C in optimized conditions with $H_2O$ as co-reactant. However, $HfCp_2Me_2$ and $ZrCp_2Me_2$ both have the drawback of being solid products at room temperature ($HfCp_2Me_2$ melting point is 57.5° C.). This makes inconvenient their use by IC makers.

In U.S. Pat. No. 6,743,473, Parkhe et al. disclose the use of $(Cp(R)_n)_xMH_{y-x}$, to make a metal and/or a metal nitride layer, where M is selected from tantalum, vanadium, niobium and hafnium, Cp is cyclopentadienyl, R is an organic group. Only examples of tantalum and niobium cyclopentadienyl compounds are disclosed. However, no liquid precursor or a precursor having a melting point lower than 50° C. is disclosed.

Today, there is a need for providing liquid or low melting point (<50° C.) group IV precursor compounds, and in particular Hf and Zr compounds, that would allow simultaneously:

proper distribution (physical state, thermal stability at distribution temperatures), wide self-limited ALD window, deposition of pure films either by ALD or MOCVD.

DISCLOSURE

According to the invention, certain cyclopentadienyl or pentadienyl based group IV metal-organic precursors have been found suitable for the deposition of Group IV metal containing thin films by either ALD or MOCVD processes and have the following advantages:

They are liquid at room temperature or having a melting point lower than 50° C., They are thermally stable to enable proper distribution (gas phase or direct liquid injection) without particles generation, They are thermally stable to allow wide self-limited ALD window, 4) allowing deposition of a variety of Group IV metals containing films, including ternary or quaternary materials, by using one or a combination of co-reactants (selected from the group comprising of $H_2$, $NH_3$, $O_2$, H$_2$O, O$_3$, SiH$_4$, Si$_2$H$_6$, Si$_3$H$_8$, TriDMAS, BDMAS, BDEAS, TDEAS, TDMAS, TEMAS, (SiH$_3$)$_3$N, (SiH$_3$)$_2$O, TMA or an aluminum-containing precursor, TBTDET, TAT-DMAE, PET, TBTDEN, PEN, lanthanide-containing precursors such as Ln(tmhd)$_3$ . . . ).

According to the invention, there is provided a method of forming on at least one substrate at least one metal containing dielectric film having the formula (M$^1_{1-a}$ M$^2_a$) O$_b$ N$_c$, wherein:

0≦a<1
0<b≦3, preferably 1.5≦b≦2.5
0≦c≦1, preferably 0≦c≦0.5
M$^1$ and M$^2$ being metals
said method comprising the steps of:
(a) providing a substrate into a reactor
(b) introducing into said reactor at least one metal containing precursor having the formula:

$$(R_yOp)_x(R_tCp)_zM^1R'_{4-x-z}$$

wherein:
M$^1$=Hf, Zr and/or Ti;
(R$_y$Op) represents one pentadienyl (Op) ligand, substituted or not, with y R substituents in any position on Op;
(R$_t$Cp) represents one cyclopentadienyl (Cp) ligand, substituted or not with t R substituents in any position on Cp;
Each R substituting a pentadienyl or each R substituting a cyclopentadienyl is a ligand independently selected from the group consisting of Cl, C1-C4 linear or branched, alkyl, alkylamides, alkoxide, alkylsilylamides, amidinates, carbonyl, each R being similar to or different from other R substituting the pentadienyl and other R substituting the cyclopentadienyl;
Each R' is a ligand independently selected from the group consisting of H, Cl, C1-C4 linear or branched, alkyl, alkylamides, alkoxide, alkylsilylamides, amidinates, carbonyl, each R' being similar or different.
x is an integer representing the number of pentadienyl ligands, substituted or not;
z is an integer representing the number of cyclopentadienyl ligands, substituted or not;
y is an integer representing the number of substituents on each Op, and is independent selected for each Op;
t is an integer representing the number of substituents on each Cp, and is independent selected for each Cp;
0≦x≦3, preferably x=0 or 1;
0≦z≦3, preferably z=2;
0≦y≦7, preferably y=2 and in this case each R is a methyl group;
0≦t≦5, preferably t=1 and R is a methyl group;
Unspecified substituents to Cp or Op ligands are H by default.
(c) optionally introducing at least one M$^2$ containing precursor, M$^2$ being selected from the group essentially consisting of Mg, Ca, Zn, B, Al, In, Lanthanides (Sc, Y, La and rare earths), Si, Ge, Sn, Ti, Zr, Hf, V, Nb, Ta;
(d) providing at least one oxygen containing and/or nitrogen containing fluid into said reactor;
(e) reacting said at least one metal containing precursor with said at least one oxygen containing and/or nitrogen containing fluid;
(f) depositing said (M$^1_{1-a}$ M$^2$a) O$_b$ N$_c$, film onto said substrate at a temperature comprised between 100° C. to 500° C., preferably between 150° C. and 350° C.,
provided that when a=0, b=2, c=0, x=0, z=2, at least one t on at least one Cp is different from zero.

The oxygen containing fluids shall be preferably selected from the group consisting of O$_2$, O$_3$, H$_2$O, H$_2$O$_2$, oxygen-containing radicals such as O. or OH. and mixtures thereof, while the nitrogen-containing fluids shall be selected from the group consisting of N$_2$, NH$_3$, hydrazine and its alkyl or aryl derivatives, nitrogen-containing radicals such as N., NH., NH$_2$. and mixtures thereof.

According to one embodiment when both nitrogen and oxygen are needed, the oxygen and nitrogen-containing fluids may be selected from the group consisting of NO, NO$_2$, N$_2$O, N$_2$O$_5$, N$_2$O$_4$ and mixtures thereof, (selecting one of those fluids automatically generate an oxynitride layer, with a certain ration of N/O molecules. If the certain ratio is not appropriate, then another nitrogen containing fluid and/or another oxygen containing fluid is needed.

To carry out the process of the invention, the pressure shall be comprised between 1 Pa and 100000 Pa, preferably between 25 Pa and 1000 Pa.

The various reactants can be introduced into the reactor either simultaneously (chemical vapor deposition), sequentially (atomic layer deposition) or different combinations thereof (one example is to introduce e.g. the two metal sources together in one pulse and the oxygen gas in a separate pulse (modified atomic layer deposition); another example is to introduce oxygen continuously and to introduce metal source by pulse (pulsed chemical vapor deposition)).

According to another embodiment the method according to the invention may further comprise the step of (g) providing at least one metal containing precursor containing at least one of the following precursors: M$^1$(NMe$_2$)$_4$, M$^1$(NEt$_2$)$_4$, M$^1$(NMeEt)$_4$, M$^1$(mmp)$_4$, M$^1$(OtBu)$_4$, M$^1$(OtBu)$_2$(mmp)$_2$ and mixtures thereof.

Preferably, the at least one metal containing precursor introduced in step b) defined here above shall have a melting point below 50° C., preferably below 35° C. while more preferably the at least one metal containing precursor shall be liquid at room temperature.

The method according to the invention may also further comprises the step of:
(h) mixing together at least two different metal containing precursors A and B to provide a precursor mixture, A being (R$_y$Op)$_x$(R$_t$Cp)$_z$M$^1$R'$_{4-x-z}$ and B being selected from the group consisting of (R$_y$Op)$_x$(R$_t$Cp)$_z$M$^1$R'$_{4-x-z}$, M$^1$(NMe$_2$)$_4$, M$^1$(NEt$_2$)$_4$, M$^1$(NMeEt)$_4$, M$^1$(mmp)$_4$, M$^1$(OtBu)$_4$, M$^1$(OtBu)$_2$(mmp)$_2$ and mixtures thereof, and
(i) providing said metal precursor mixture into said reactor.

According to an alternative method of the invention, step (h) and (i) as defined above are carried out instead of step (b).

According to another embodiment of the invention, to form an M$^1$oxyde containing film wherein a=0, b being equal to about 2 and c=0, the metal containing precursor of steps (b) and/or (h) is selected from the group consisting of: HfCp$_2$Cl$_2$, Hf(MeCp)$_2$Me$_2$, HfCp(MeCp)Cl$_2$, Hf(MeCp)$_2$Cl$_2$, HfCp(MeCp)Me$_2$, Hf(EtCp)(MeCp)Me$_2$, Hf(EtCp)$_2$Me$_2$, Hf(MeCp)$_2$(CO)$_2$, ZrCP$_2$Cl$_2$, Zr(MeCp)$_2$Me$_2$, ZrCp(MeCp)Cl$_2$, Zr(MeCp)$_2$Cl$_2$, ZrCp(MeCp)Me$_2$, Zr(EtCp)(MeCp)Me$_2$, Zr(EtCp)$_2$Me$_2$, Zr(MeCp)$_2$(CO)$_2$ and mixtures thereof.

According to still another embodiment of the invention, to form an M$^1$oxynitride-containing dielectric film wherein a=0, 1.5≦b≦2.5 and 0<c≦0.5, the metal containing precursor of step (b) and/or (h) shall be selected from the group consisting of HfCP$_2$Cl$_2$, Hf(MeCp)$_2$Me$_2$, HfCp(MeCp)Cl$_2$, Hf(MeCp)$_2$Cl$_2$, HfCp(MeCp)Me$_2$, Hf(EtCp)(MeCp) Me$_2$, Hf(EtCp)$_2$Me$_2$, Hf(MeCp)$_2$(CO)$_2$, ZrCP$_2$Cl$_2$, $Zr(MeCp)_2Me_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$ and mixture thereof.

According to another embodiment of the invention to form an $M^1M^2$ Oxide containing dielectric film wherein $0 \leq a < 1$ and $c=0$, the metal containing precursor of step (b) and/or (h) shall be selected from the group consisting of $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, the $M^2$ containing precursor of step (c) being introduced into the reactor, said precursor being preferably selected from the group consisting of Si, Mg, lanthanides (i.e. Sc, Y and rare earths) and/or Ta.

According to another different embodiment of the invention, the $M^2$ containing precursor is selected from the group consisting of disiloxane, trisilylamine, disilane, trisilane, a alkoxysilane $SiH_x(OR^1)_{4-x}$, silanol $Si(OH)_x(OR^1)_{4-x}$ (preferably $Si(OH)(OR^1)_3$; more preferably $Si(OH)(OtBu)_3$), aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$; BTBAS $SiH_2(NHtBu)_2$); BDEAS $SiH_2(NEt_2)_2$) and mixtures thereof (or their germanium equivalents), trimethylaluminum, dimethylaluminum hydride, alkoxyalane $AlR^i_x(OR')_{3-x}$ (where x is comprised between 0 and 4; each $R^i$ is independently H or a C1-C6 carbon chain, either linear, branched or cyclic; preferably $AlR^1R^2(OR')$, with $R^1$ and $R^2$ are independently H or a C1-C6 carbon chain, either linear, branched or cyclic, most preferably $AlMe_2(OiPr)$), amidoalane $AlR^i_x(NR'R'')_{3-x}$ (where x is comprised between 0 and 3; each $R^i$ is independently H or a C1-C6 carbon chain, either linear, branched or cyclic), $Ta(OMe)_5$, $Ta(OEt)_5$, $Ta(OR^1)_4(O-C(R^2)(R^3)-CH_2-OR^4)$ (each $R^i$ is independently H or a C1-C6 carbon chain, either linear, branched or cyclic, preferably TAT-DMAE $Ta(OEt)(OCMe_2CH_2-OMe))$, $Ta(OR^1)_4(O-C(R^2)(R^3)-CH_2-N(R^4)(R^5))$ (each $R^i$ is independently H or a C1-C6 carbon chain, either linear, branched or cyclic, $Ta(NMe_2)_5$, $Ta(NEt_2)_4$, $Ta(NEt_2)_5$, $Ta(=NR^1)(NR^2R^3)_3$ (each $R^1$, $R^2$ and $R^3$ are independently H or a C1-C6 carbon chain, either linear, branched or cyclic and where the amino ligand can have different substituant), $Nb(OMe)_5$, $Nb(OEt)_5$, $Nb(OR^1)_4(O-C(R^2)(R^3)-CH_2-OR^4)$ (each $R^i$ is independently H or a C1-C6 carbon chain, either linear, branched or cyclic, preferably NBT-DMAE $Nb(OEt)(OCMe_2CH_2-OMe))$, $Nb(OR^1)_4(O-C(R^2)(R^3)-CH_2-N(R^4)(R^5))$ (each $R^1$ is independently H or a C1-C6 carbon chain, either linear, branched or cyclic, $Nb(NMe_2)_5$, $Nb(NEt_2)_4$, $Nb(NEt_2)_5$, $Nb(=NR^1)(NR^2R^3)_3$ (each $R^1$, $R^2$ and $R^3$ are independently H or a C1-C6 carbon chain, either linear, branched or cyclic and where the amino ligand can have different substituant), a lanthanide metal source (Sc, Y, La, Ce, Pr, Nd, Gd . . . ), a source with at least one β-diketonate ligand, such as having the form of $Ln(-O-C(R^1)-C(R^2)-C(R^3)-O-)(-O-C(R^4)-C(R^5)-C(R^6)-O-)(-O-C(R^7)-C(R^8)-C(R^9)-O-)$ where each $R^i$ is independently H or a C1-C6 carbon chain, either linear, branched or cyclic), or of the form of a cyclopentadienyl lanthanide $Ln(R^1Cp)(R^2Cp)(R^3CP)$ (where each $R^i$ is independently H or a C1-C6 carbon chain, either linear, branched or cyclic), $Ln(NR^1R^2)(NR^3R^4)(NR^5R^6)$ (where each $R^i$ is bonded to nitrogen and is independently H or a C1-C6 carbon chain, either linear, branched or cyclic or an alkylsilyl chain of the form $SiR^7R^8R^9$ where each $R^i$ is bonded to silicon and is independently H or a C1-C4 carbon chain, either linear, branched or cyclic), a divalent metal A (preferably Mg, Ca, Zn) of the form $A(-O-C(R^1)-C(R^2)-C(R^3)-O-)(-O-C(R^4)-C(R^5)-C(R^6)-O-)$ (where each $R^i$ is independently H or a C1-C6 carbon chain, either linear, branched or cyclic) or of the form of a cyclopentadienyl lanthanide $A(R^1Cp)(R^2Cp)$ (where each $R^i$ is independently H or a C1-C6 carbon chain, either linear, branched or cyclic).

According to an embodiment of the invention, to form an $M^1M^2$ oxynitride containing dielectric film wherein $0 \leq a < 1$ and $0 < c \leq 0.5$, the metal containing precursor of step (b) and/or (h) shall be selected from the group consisting of $HfCP_2Cl_2$, $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(EtCp)_2Me_2$, $Hf(MeCp)_2(CO)_2$, $ZrCP_2Cl_2$, $Zr(MeCp)_2Me_2$, $ZrCp(MeCp)Cl_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$, the $M^2$ containing precursor of step (c) being introduced into the reactor, said $M^2$ precursor being preferably selected from the group consisting of Si, Mg, lanthanides (i.e. Sc, Y and rare earths) and/or Ta, and wherein in step (d) at least one oxygen containing precursor and at least one nitrogen containing precursor is introduced into the reactor.

Preferably, when $M^1M^2$ oxynitride are deposited, the $M^2$ containing precursor is selected from the group consisting of disiloxane, trisilylamine, disilane, trisilane, a alkoxysilane $SiH_x(OR^1)_{4-x}$, a silanol $Si(OH)_x(OR^1)_{4-x}$ (preferably $Si(OH)(OR^1)_3$, more preferably $Si(OH)(OtBu)_3$ an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$, BTBAS $SiH_2(NHtBu)_2$); BDEAS $SiH_2(NEt_2)_2$) and mixtures thereof (or their germanium equivalents), trimethylaluminum, dimethylaluminum hydride, an alkoxyalane $AlR^i_x(OR')_{3-x}$ (where x is comprised between 0 and 4; $R^1$ and $R^2$ are independently H or a C1-C6 carbon chain, either linear, branched or cyclic; preferably $AlR^1R^2(OR')$, most preferably $AlMe_2(OiPr)$), an amidoalane $AlR^i_x(NR'R'')_{3-x}$ (where x is comprised between 0 and 4; $R^1$ and $R^2$ are independently H or a C1-C6 carbon chain, either linear, branched or cyclic), $Ta(OMe)_5$, $Ta(OEt)_5$, $Ta(OR^1)_4(O-C(R^2)(R^3)-CH_2-OR^4)$ (each $R^i$ is independently H or a C1-C6 carbon chain, either linear, branched or cyclic, preferably TAT-DMAE $Ta(OEt)(OCMe_2CH_2-OMe))$, $Ta(OR^1)_4(O-C(R^2)(R^3)-CH_2-N(R^4)(R^5))$ (each $R^i$ is independently H or a C1-C6 carbon chain, either linear, branched or cyclic, $Ta(NMe_2)_5$, $Ta(NEt_2)_4$, $Ta(NEt_2)_5$, $Ta(=NR^1)(NR^2R^3)_3$ (each $R^1$ and $R^2$ are independently H or a C1-C6 carbon chain, either linear, branched or cyclic and where the amino ligand can have different substituant), $Nb(OMe)_5$, $Nb(OEt)_5$, $Nb(OR^1)_4(O-C(R^2)(R^3)-CH_2-OR^4)$ (each $R'$ is independently H or a C1-C6 carbon chain, either linear, branched or cyclic, preferably NBT-DMAE $Nb(OEt)(OCMe_2CH_2-OMe))$, $Nb(OR^1)_4(O-C(R^2)(R^3)-CH_2-N(R^4)(R^5))$ (each $R^i$ is independently H or a C1-C6 carbon chain, either linear, branched or cyclic, $Nb(NMe_2)_5$, $Nb(NEt_2)_4$, $Nb(NEt_2)_5$, $Nb(=NR^1)(NR^2R^3)_3$ (each $R^1$, $R^2$ and $R^3$ are independently H or a C1-C6 carbon chain, either linear, branched or cyclic and where the amino ligand can have different substituant), a lanthanide metal source (Sc, Y, La, Ce, Pr, Nd, Gd . . . ) source with at least one β-diketonate ligand, such as of the form $Ln(-O-C(R^1)-C(R^2)-C(R^3)-O-)(-O-C(R^4)-C(R^5)-C(R^6)-O-)(-O-C(R^7)-C(R^8)-C(R^9)-O-)$ where each $R^i$ is independently H or a C1-C6 carbon chain, either linear, branched or cyclic), or of the form of a cyclopentadienyl lanthanide $Ln(R^1Cp)(R^2Cp)(R^3CP)$ (where each $R^i$ is independently H or a C1-C6 carbon chain, either linear, branched or cyclic), $Ln(NR^1R^2)(NR^3R^4)(NR^5R^6)$ (where each $R^i$ is bonded to nitrogen and is independently H or a C1-C6 carbon chain, either linear, branched or cyclic or an alkylsilyl chain of the form $SiR^7R^8R^9$ where each $R^i$ is bonded to silicon and is independently H or a C1-C4 carbon chain, either linear, branched or cyclic), a divalent metal A (preferably Mg, Ca, Zn) of the form $A(—O—C(R^1)—C(R^2)—C(R^3)—O—)(—O—C(R^4)—C(R^5)—C(R^6)—O—)$ (where each $R^i$ is independently H or a C1-C6 carbon chain, either linear, branched or cyclic) or of the form of a cyclopentadienyl lanthanide $A(R^1Cp)(R^2Cp)$ (where each $R^i$ is independently H or a C1-C6 carbon chain, either linear, branched or cyclic).

The invention also may generally relates to the use of $(R_yOp)_x(R_tCp)_zM^1R'_{4-x-z}$ to make dielectric films e.g. for integrated circuits or Metal Insulator Metal (MIM) architectures for Random Access Memories.

According to still another aspect, the invention relates also to new precursors comprising composition for semi-conductor or RAM manufacture, said precursor having the formula:

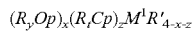

wherein $M^1$=Hf, Zr and/or Ti $(R_yOp)$ represents one pentadienyl (Op) ligand, substituted or not, with y R substituents in any position on Op;

$(R_tCp)$ represents one cyclopentadienyl (Cp) ligand, substituted or not, with t R substituents in any position on Cp;

Each R substituting a pentadienyl or R substituting a cyclopentadienyl are organics independently selected from the group consisting of Cl, C1-C4 linear or branched, alkyl, alkylamides, alkoxide, alkylsilylamides, amidinates, carbonyl, each $R_y$ or each $R_t$ being similar to or different from other $R_y$ or other $R_t$, respectively;

Each R' is an organics independently selected from the group consisting of H, Cl, C1-C4 linear or branched, alkyl, alkylamides, alkoxide, alkylsilylamides, amidinates, carbonyl, each R' being similar or different.

x is an integer representing the number of pentadienyl ligand, substituted or not z is an integer representing the number of cyclopentadienyl ligand, substituted or not;

y is an integer representing the number of substituents on each Op, and is independent by selected for each Op;

t is an integer representing the number of substituents on each Cp, and is independent selected for each Cp;

$0 \leq x \leq 3$, preferably x=0 or 1;

$0 \leq z \leq 3$, preferably z=2;

$0 \leq y \leq 7$, preferably y=2 and in this case each R is methyl;

$0 \leq t \leq 5$, preferably t=1 and R is a methyl group;

Unspecified substituents to Cp or Op ligands are H by default;

All R' are not simultaneously equal to H when x=0, provided that when a=0, b=2, c=0, x=0, z=2, at least one t on at least one Cp is different from 0.

According to another embodiment, such new precursor composition may further comprise a second metal containing precursor, different from the first metal precursor, said second metal containing precursor being selected from the group consisting of $(R_yOp)_x(R_tCp)_zM^1R'_{4-x-z}$, $M^1(NMe_2)_4$, $M^1(NEt_2)_4$, $M^1(NEtMe)_4$, $M^1(mmp)_4$, $M^1(OtBu)_4$, $M^1(OtBu)_2(mmp)_2$ and mixtures thereof.

DETAILED DESCRIPTION

Example I

Deposition of Metal Oxide Film $M^1O_2$ with $M^1$ being Preferably Hafnium and Zirconium The film to be deposited relates to the case where a=0, b is about 2 and c=0.

To make the deposition of such film on the surface of a wafer or in a deep trench to manufacture MIM structures for DRAM, one need to vaporize the $M^1$ metal source as defined in steps (b) and/or (h) here above into the reactor (preferably Hafnium or Zirconium), inject an oxygen source, preferably moisture, oxygen or ozone into said reactor, react the products at appropriate temperature (preferably between 150° C. and 350° C.) and pressure (preferably between 25 Pa and 1000 Pa) for the duration necessary to achieve either a thin film deposition on the substrate or to fill out deep trenches by ALD or pulse CVD process (sequential pulse injection of metal sources are necessary in order to allow regular deposition of the oxide in the trench to progressively fill out this trench and provide no voids in the dielectric film and therefore no defect in the capacitor dielectric film).

The dielectric film shall have the desired final composition (here essentially variations of the b value around 2 modifying the ratio of precursor to oxygen source).

It is possible to select the $M^1$ containing precursors from the three following options, a, b or c:

a) $M^1$ source is a molecule or a mixture of molecules having the formula $(R_tCp)_zM^1R'_{4-z}$, wherein:

$M^1$ is a group IV metal selected from the group consisting of Hf, Zr, Ti or mixture thereof.

z is an integer comprised between 1 and 3, preferably z=2.

t is an integer between 0 and 5, preferably t=1.

Cp is a cyclopentadienyl ligand. Each Cp comprises t substituents R

Each R substituting a cyclopentadienyl is a ligand independently selected from the group consisting of Cl, C1-C4 linear or branched, alkyl, alkylamides, alkoxide, alkylsilylamides, amidinates, carbonyl, isonitrile, each R being similar to or different from other R substituting the cyclopentadienyl;

Each R' is a ligand independently selected from the group consisting of H, Cl, C1-C4 linear or branched, alkyl, alkylamides, alkoxide, alkylsilylamides, amidinates, carbonyl, each R' being similar or different from other R'.

When one or several Cp ligands are present in the molecule, the number of substituents on each Cp can be different, their substituents (R) can be different and in whatever position on each Cp.

The preferred molecule is $M(RCp)_2Me_2$. More preferably R is Me or Et, while the molecule is preferably selected from the group of molecules having melting point lower than 35° C., more preferably which is liquid or which can be easy liquefied for easy delivery.

Delivery of molecules in liquid form is usually carried out by bubbling an inert gas ($N_2$, He, Ar, ... ) into the liquid and providing the inert gas plus liquid gas mixture to the reactor.

The formula of the molecule is shown below:

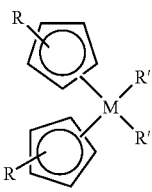

b) The $M^1$ metal source is a molecule or mixture of molecules having the general formula: $(R_yOp)_x M^1R'_{4-x}$, wherein:

$M^1$ is a group IV metal (Hf, Zr, Ti).

x is an integer comprised between 1 and 3, preferably, x=2.

y is an integer between 1 and 7. Preferentially y=2.

Op is a pentadienyl ligand. Each Op comprises y substituents R.

R and R' are organic ligand independently selected from the group consisting of H, Cl, C1-C4 linear or branched, alkyl, alkylamides, alkoxide, alkylsilylamides, amidinates, carbonyl, isonitrile. If several Op ligands are present in the molecule, the number of substituents can be similar or different, their substituents (R) can be different and in whatever position. Each R substituting a pentadienyl may be similar or different from other R also substituting a pentadienyl, either the same or a different one. Each R' may be similar or different from other R'. Each Op may comprise one or several R.

The molecule is preferably $M^1(2,4-R_2Op)_2Me_2$. More preferably R is Me (i.e. metal dimethyl bis(2,4-dimethylpentadienyl)).

The molecule has a melting point lower than 50° C. The molecule has preferably a melting point lower than 35° C., i.e. which is liquid or can be easy liquefied for easy delivery.

The general formula of the molecule is:

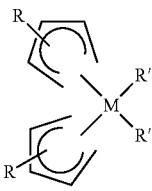

with one or several (y times) R on each Op cycle.

c) The $M^1$ metal source is a molecule or mixture of molecules having the general formula: $(R_yOp)_x(R_tCp)_zM^1R'_{4-x-z}$, wherein:

$M^1$ is a group IV metal (Hf, Zr, Ti).

x and z are integers comprised between 1 and 3, preferably x=1, and z=1.

y and t are integers between 1 and 7, preferably y=2 and t=1.

Cp is a cyclopentadienyl ligand. Each Cp comprises t substituents R.

Op is a pentadienyl ligand. Each Op comprises y substituents R.

Each R substituting a pentadienyl and each R substituting a cyclopentadienyl, and R' are ligands independently selected from the group consisting of H, Cl, C1-C4 linear or branched, alkyl, alkylamides, alkoxide, alkylsilylamides, amidinates, carbonyl, isonitrile. Each R substituting a pentadienyl may be similar or different from other R substituting a pentadienyl, (either on the same or on a different one), or a cyclopentadienyl. Each R substituting a cyclopentadienyl may be similar or different from other R substituting a cyclopentadienyl, (either the same or on a different one), or a pentadienyl. Each Op and/or Cp may have one or several R substituents. If several Op ligands are present in the molecule, the number of substituents can be similar or different, their substituents (R) can be different. The same applies for the substituents R on Cp.

The molecule is preferably $M(RCp)(2,4-R_2Op)Me_2$. More preferably R substituting the cyclopentadienyl and the R's substituting the pentadienyl are Me (i.e. metal dimethyl(2,4-dimethylpentadienyl)(methylcylopentadienyl)).

The molecule has preferably a melting point lower than 35° C., i.e. which is liquid or can be easy liquefied for easy delivery.

The general formula of the molecule is:

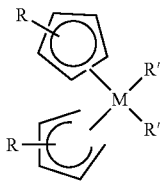

The oxygen source shall be preferably, without limitations, oxygen ($O_2$), oxygen radicals (for instance O. or OH.), such as radicals generated by a remote plasma system, ozone, NO, $N_2O$, $NO_2$, moisture ($H_2O$) and $H_2O_2$.

Regarding the deposition process by itself, the reactants can be introduced into the reactor simultaneously (chemical vapor deposition), sequentially (atomic layer deposition) or different combinations (one example is to introduce metal source and the other metal source together in one pulse and oxygen in a separate pulse [modified atomic layer deposition]; another option is to introduce oxygen continuously and/or to introduce the metal source by pulse (pulsed-chemical vapor deposition).

Example II

Deposition of Metal Oxynitride Films $M^1ON$ with $M^1$ being Preferably Hafnium and Zirconium The film deposited relates to the case where a=0 and b and c are different from zero.

All the information given in Example I is applicable in this Example II, except that nitrogen needs to be introduced into the reactor.

The nitrogen shall be selected from a nitrogen source selected from the group comprising nitrogen ($N_2$), ammonia, hydrazine and alkyl derivatives, N-containing radicals (for instance N., NH., $NH_2$.), NO, $N_2O$, $NO_2$ or the like.

Example III

Deposition of $M^1M^2$ Metal Oxide Films with $M^1$ being Preferably Hf or Zr and $M^2$ being Preferably Si or Al The film deposited on the substrate in this example illustrates the case wherein a≠0, b≠0 and c=0.

All the information given in Example I are applicable in this Example III, except that a $M^2$ metal source is additionally needed.

The $M^2$ containing precursor is also introduced into the reactor to crate the $M^2$ source of metal. This $M^2$ containing precursor source shall be preferably:

a) a silicon (or germanium) source and is selected from, but not limited to, the group consisting of disiloxane, trisilylamine, disilane, trisilane, a alkoxysilane $SiH_x(OR^1)_{4-x}$, a silanol $Si(OH)_x(OR^1)_{4-x}$ (preferably $Si(OH)(OR^1)_3$; more preferably $Si(OH)(OtBu)_3$ an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$; BTBAS $SiH_2(NHtBu)_2$) BDEAS $SiH_2(NEt_2)_2$) and mixtures thereof (or their germanium equivalent); or b) an aluminum source selected from the group comprising trimethylaluminum, dimethylaluminum hydride, an alkoxyalane $AlR^i_x(OR')_{3-x}$ (where x is comprised between 0 and 4; $R^1$ and $R^2$ are independently H or a C1-C6 carbon chain, either linear, branched or cyclic; preferably $AlR^1R^2(OR')$, most preferably $AlMe_2(OiPr)$), an amidoalane $AlR^i_x(NR'R'')_{3-x}$ (where x is comprised between 0 and 4; $R^1$ and $R^2$ are independently H or a C1-C6 carbon chain, either linear, branched or cyclic) and mixtures thereof; or c) a tantalum (or niobium) source selected from the group comprising $Ta(OMe)_5$, $Ta(OEt)_5$, $Ta(OR^1)_4(O-C(R^2)(R^3)-CH_2-OR^4)$ (each $R^i$ is independently H or a C1-C6 carbon chain, either linear, branched or cyclic, preferably TATDMAE $Ta(OEt)(OCMe_2CH_2-OMe)$), $Ta(OR^1)_4(O-C(R^2)(R^3)-CH_2-N(R^4)(R^5))$ (each $R^i$ is independently H or a C1-C6 carbon chain, either linear, branched or cyclic, $Ta(NMe_2)_5$, $Ta(NEt_2)_4$, $Ta(NEt_2)_5$, $Ta(=NR^1)(NR^2R^3)_3$ (each $R^1$ and $R^2$ are independently H or a C1-C6 carbon chain, either linear, branched or cyclic and where the amino ligand can have different substituant) and mixtures thereof; or their niobium counterparts.

d) a lanthanide metal source (Sc, Y, La, Ce, Pr, Nd, Gd . . . ) source with at least one β-diketonate ligand, such as of the form $Ln(-O-C(R^1)=C(R^2)-C(R^3)-O-)(-O-C(R^4)-C(R^5)-C(R^6)-O-)(-O-C(R^7)-C(R^8)-C(R^9)-O-)$ where each $R^i$ is independently H or a C1-C6 carbon chain, either linear, branched or cyclic), or of the form of a cyclopentadienyl lanthanide $Ln(R^1Cp)(R^2Cp)(R^3CP)$ (where each $R^i$ is independently H or a C1-C6 carbon chain, either linear, branched or cyclic), $Ln(NR^1R^2)(NR^3R^4)(NR^5R^6)$ (where each $R^i$ is bonded to nitrogen and is independently H or a C1-C6 carbon chain, either linear, branched or cyclic or an alkylsilyl chain of the form $SiR^7R^8R^9$ where each $R^i$ is bonded to silicon and is independently H or a C1-C4 carbon chain, either linear, branched or cyclic)

e) a IVA metal source with $M^2$ is similar or different from $M^1$ but in which the $M^2$ source is different from the $M^1$ metal source introduced in step b) in the reactor, said IVA metal source being selected from $(R_yOp)_x(R_tCp)_zM^1R'_{4-x-z}$, $M^1(OR^1)_4$ or other alkoxide-containing metal sources, $M(NR^1R^2)_4$, or adducts containing these species.

f) a divalent metal (preferably Mg, Ca, Zn) selected from the group comprising metal β-diketonates or adducts containing these species.

The invention is directed to the deposition of dielectric films (formula $(M^1_{1-a} M^2_a) O_b N_c$) onto a support such as a wafer, in a reactor using ALD, CVD, MOCVD, pulse CVD processes.

Example IV

Deposition of $M^1M^2$ Metal Oxynitride Films with $M^1$ being Preferably Hf or Zr and $M^2$ being Preferably Si or Al The film deposited on the substrate in this example illustrates the case wherein a≠0, b≠0 and c≠0.

All the information given in Example III is applicable in this case, except that nitrogen needs to be introduced into the reactor.

The nitrogen source shall be selected from the group comprising nitrogen (N2), ammonia, hydrazine and alkyl derivatives, N-containing radicals (for instance N., NH., $NH_2$.), NO, $N_2O$, $NO_2$.

Example V

Examples of New Group IV Precursors for Group IV Metal Containing Thin Film Deposition $Hf(iPrCp)_2H_2$, $Hf(nPrCp)_2H_2$, $Hf(EtCp)_2H_2$, $Hf(MeCp)_2Me_2$, $Hf(EtCp)_2Me_2$, $Hf(MeCp)_2EtMe$, $Hf(EtCp)_2EtMe$, $Hf(MeCp)_2nPrMe$, $Hf(MeCp)_2Et_2$, $Hf(MeCp)(EtCp)Me_2$, $Hf(MeCp)(EtCp)EtMe$, $Hf(iPrCp)_2EtMe$, $Hf(Me_2Cp)_2Me_2$, $Hf(Et_2Cp)_2Me_2$, $Hf(MeCp)(MeOp)Me_2$, $Hf(EtCp)(MeOp)Me_2$, $Hf(MeCp)(EtOp)Me_2$, $Hf(MeCp)(MeOp)EtMe$, $Hf(iPrOp)_2H_2$, $Hf(nPrOp)_2H_2$, $Hf(EtOp)_2H_2$, $Hf(MeOp)_2Me_2$, $Hf(EtOp)_2Me_2$, $Hf(MeOp)_2EtMe$, $Hf(EtOp)_2EtMe$, $Hf(MeOp)_2nPrMe$, $Hf(MeOp)_2Et_2$, $Hf(MeOp)(EtOp)Me_2$, $Hf(MeOp)(EtOp)EtMe$, $Hf(iPrOp)_2EtMe$, $Hf(Me_2Op)_2Me_2$, $Hf(Et_2Op)_2Me_2$, $Hf(C_5Me_5)_2Me_2$, $Hf(MeCp)_2Cl_2$, $Hf(EtCp)_2Cl_2$, $Hf(iPrCp)_2Cl_2$, $Hf(MeCp)(EtCp)Cl_2$, HfCp(MeCp)$Cl_2$, $Hf(MeOp)_2Cl_2$, $Hf(EtOp)_2Cl_2$, $Hf(iPrOp)_2Cl_2$, $Hf(MeOp)(EtOp)Cl_2$, $HfOp(MeOp)Cl_2$, $Zr(iPrCp)_2H_2$, $Zr(nPrCp)_2H_2$, $Zr(EtCp)_2H_2$, $Zr(MeCp)_2Me_2$, $Zr(EtCp)_2Me_2$, $Zr(MeCp)_2EtMe$, $Zr(EtCp)_2EtMe$, $Zr(MeCp)_2nPrMe$, $Zr(MeCp)_2Et_2$, $Zr(MeCp)(EtCp)Me_2$, $Zr(MeCp)(EtCp)EtMe$, $Zr(iPrCp)_2EtMe$, $Zr(Me_2Cp)_2Me_2$, $Zr(Et_2Cp)_2Me_2$, $Zr(MeCp)(MeOp)Me_2$, $Zr(EtCp)(MeOp)Me_2$, $Zr(MeCp)(EtOp)Me_2$, $Zr(MeCp)(MeOp)EtMe$, $Zr(iPrOp)_2H_2$, $Zr(nPrOp)_2H_2$, $Zr(EtOp)_2H_2$, $Zr(MeOp)_2Me_2$, $Zr(EtOp)_2Me_2$, $Zr(MeOp)_2EtMe$, $Zr(EtOp)_2EtMe$, $Zr(MeOp)_2nPrMe$, $Zr(MeOp)_2Et_2$, $Zr(MeOp)(EtOp)Me_2$, $Zr(MeOp)(EtOp)EtMe$, $Zr(iPrOp)_2EtMe$, $Zr(Me_2Op)_2Me_2$, $Zr(Et_2Op)_2Me_2$, $Zr(C_5Me_5)_2Me_2$, $Zr(MeCp)_2Cl_2$, $Zr(EtCp)_2Cl_2$, $Zr(iPrCp)_2Cl_2$, $Zr(MeCp)(EtCp)Cl_2$, ZrCp(MeCp)$Cl_2$, $Zr(MeOp)_2Cl_2$, $Zr(EtOp)_2Cl_2$, $Zr(iPrOp)_2Cl_2$, $Zr(MeOp)(EtOp)Cl_2$, $ZrOp(MeOp)Cl_2$, $Ti(iPrCp)_2H_2$, $Ti(nPrCp)_2H_2$, $Ti(EtCp)_2H_2$, $Ti(MeCp)_2Me_2$, $Ti(EtCp)_2Me_2$, $Ti(MeCp)_2EtMe$, $Ti(EtCp)_2EtMe$, $Ti(MeCp)_2nPrMe$, $Ti(MeCp)_2Et_2$, $Ti(MeCp)(EtCp)Me_2$, $Ti(MeCp)(EtCp)EtMe$, $Ti(iPrCp)_2EtMe$, $Ti(Me_2Cp)_2Me_2$, $Ti(Et_2Cp)_2Me_2$, $Ti(MeCp)(MeOp)Me_2$, $Ti(EtCp)(MeOp)Me_2$, $Ti(MeCp)(EtOp)Me_2$, $Ti(MeCp)(MeOp)EtMe$, $Ti(iPrOp)_2H_2$, $Ti(nPrOp)_2H_2$, $Ti(EtOp)_2H_2$, $Ti(MeOp)_2Me_2$, $Ti(EtOp)_2Me_2$, $Ti(MeOp)_2EtMe$, $Ti(EtOp)_2EtMe$, $Ti(MeOp)_2nPrMe$, $Ti(MeOp)_2Et_2$, $Ti(MeOp)(EtOp)Me_2$, $Ti(MeOp)(EtOp)EtMe$, $Ti(iPrOp)_2EtMe$, $Ti(Me_2Op)_2Me_2$, $Ti(Et_2Op)_2Me_2$, $Ti(C_5Me_5)_2Me_2$, $Ti(MeCp)_2Cl_2$, $Ti(EtCp)_2Cl_2$, $Ti(iPrCp)_2Cl_2$, $Ti(MeCp)(EtCp)Cl_2$, TiCp(MeCp)$Cl_2$, $Ti(MeOp)_2Cl_2$, $Ti(EtOp)_2Cl_2$, $Ti(iPrOp)_2Cl_2$, $Ti(MeOp)(EtOp)Cl_2$, $TiOp(MeOp)Cl_2$, It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of forming on at least one substrate at least one metal containing dielectric film having the formula $(M^1_{1-a} M^2_a) O_b N_c$, wherein:
   $0 \leq a < 1$
   $0 < b \leq 3$,
   $0 \leq c \leq 1$,
   $M^1$ being a metal and $M^2$ being selected from the group consisting of Mg, Ca, Zn, B, Al, In, Lanthanides, Si, Ge, Sn, Ti, Zr, Hf, V, Nb, and Ta;
   said method comprising the steps of:
   (a) providing a substrate into a reactor;
   (b) introducing into said reactor at least one metal containing precursor selected from the group consisting of $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(MeCp)_2(CO)_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$ and mixtures thereof;
   (c) optionally introducing at least one $M^2$ containing precursor, $M^2$ being selected from the group consisting of Mg, Ca, Zn, B, Al, In, Lanthanides, Si, Ge, Sn, Ti, Zr, Hf, V, Nb, and Ta;
   (d) providing at least one oxygen containing and/or nitrogen containing fluid into said reactor;
   (e) reacting said at least one metal containing precursor with said at least one oxygen containing and/or nitrogen containing fluid; and
   (f) depositing said $(M^1_{1-a} M^2_a) O_b N_c$ film onto said substrate at a temperature comprised between 100 to 500° C.

2. The method of claim 1, wherein the oxygen containing fluid is selected from the group consisting of $O_2$, $O_3$, $H_2O$, $H_2O_2$, oxygen-containing radicals, and mixtures thereof.

3. The method of claim 1, wherein the nitrogen-containing fluid is selected from the group consisting of $N_2$, $NH_3$, hydrazine and its alkyl or aryl derivatives, nitrogen-containing radicals, and mixtures thereof.

4. The method of claim 1, wherein the oxygen and nitrogen-containing fluid is selected from the group consisting of NO, $NO_2$, $N_2O$, $N_2O_5$, $N_2O_4$ and mixtures thereof.

5. The method of claim 1, wherein the pressure is comprised between 1 Pa and 100 000 Pa.

6. The method of claim 1, wherein the metal containing precursor, the $M^2$ containing precursor and the oxygen containing and/or nitrogen containing fluid are introduced simultaneously into the reactor.

7. The method of claim 1, further comprising the step of providing at least one metal containing precursor containing at least one of the following precursors: $M^1(NMe_2)_4$, $M^1(NEt_2)_4$, $M^1(NMeEt)_4$, $M^1(mmP)_4$, $M^1(OtBu)_4$, $M^1(OtBu)_2(mmp)_2$ and mixtures thereof.

8. The method of claim 7, further comprising the steps of mixing together at least two different metal containing precursors A and B to provide a precursor mixture, A being selected from the group consisting of $Hf(MeCp)_2Me_2$, $HfCp(MeCp)Cl_2$, $Hf(MeCp)_2Cl_2$, $HfCp(MeCp)Me_2$, $Hf(EtCp)(MeCp)Me_2$, $Hf(MeCp)_2(CO)_2$, $Zr(MeCp)_2Cl_2$, $ZrCp(MeCp)Me_2$, $Zr(EtCp)(MeCp)Me_2$, $Zr(EtCp)_2Me_2$, $Zr(MeCp)_2(CO)_2$ and mixtures thereof and B being selected from the group consisting of $M^1(NMe_2)_4$, $M^1(NEt_2)_4$, $M^1(NMeEt)_4$, $M^1(mmp)_4$, $M^1(OtBu)_4$, $M^1(OtBu)_2(mmp)_2$ and mixtures thereof; and providing said metal precursor mixture into said reactor.

9. The method of claim 1, wherein the at least one metal containing precursor introduced in step b) has a melting point below 50° C.

10. The method of claim 9, wherein the at least one metal containing precursor is liquid at room temperature.

11. The method of claim 1, to form an $M^1$ oxide containing film wherein a=0, b being equal to about 2 and c=0.

12. The method of claim 1, to form an $M^1$ oxynitride-containing dielectric film wherein a=0, $1.5 \leq b \leq 2.5$ and $0 < c \leq 0.5$.

13. The method of claim 1, to form an $M^1M^2$ oxide containing dielectric film wherein $0 \leq a < 1$ and c=0, the $M^2$ containing precursor of step (c) being introduced into the reactor, said precursor being selected from the group consisting of Si, Mg and Ta.

14. The method of claim 13, wherein the $M^2$ containing precursor is selected from the group consisting of disiloxane, trisilylamine, disilane, trisilane, an alkoxysilane having the formula $SiH_x(OR^1)_{4-x}$, a silanol having the formula $Si(OH)_x(OR^1)_{4-x}$, an aminosilane having the formula $SiH_x(NR^1R^2)_{4-x}$, $Ta(OMe)_5$, $Ta(OEt)_5$, $Ta(OR^1)_4(O-C(R^2)(R^3)-CH_2-OR^4)$, $Ta(OR^1)_4(O-C(R^2)(R^3)-CH_2-N(R^4)(R^5))$, $Ta(NMe_2)_5$, $Ta(NEt_2)_4$, $Ta(NEt_2)_5$, $Ta(=NR^1)(NR^2R^3)_3$, an alkylsilyl chain of the form $SiR^7R^8R^9$ where each $R^i$ is bonded to silicon, a IVA metal source wherein the $M^2$ source is different from the $M^1$ metal source introduced in step b) in the reactor, said IVA metal source being selected from the group consisting of $M^1(OR^1)_4$, $M(NR^1R^2)_4$, and adducts containing these species, a divalent metal A source having the formula $A(-O-C(R^1)-C(R^2)-C(R^3)-O-)(-O-C(R^4)-C(R^5)-C(R^6)-O-)$, and a cyclopentadienyl divalent metal A source having the formula $A(R^1Cp)(R^2Cp)$, wherein each $R^i$ is independently selected from the group consisting of H and a C1-C6 carbon chain.

15. The method of claim 1, to form an $M^1M^2$ oxynitride containing dielectric film wherein $0 \leq a < 1$ and $0 < c \leq 0.5$, the $M^2$ containing precursor of step (c) being introduced into the reactor, said precursor being selected from the group consisting of Si, Mg and Ta, and wherein in step (d) at least one oxygen containing precursor and at least one nitrogen containing precursor is introduced into the reactor.

16. The method of claim 15, wherein the $M^2$ containing precursor is selected from the group consisting of disiloxane, trisilylamine, disilane, trisilane, an alkoxysilane having the formula $SiH_x(OR^1)_{4-x}$, a silanol having the formula $Si(OH)_x(OR^1)_{4-x}$, an aminosilane having the formula $SiH_x(NR^1R^2)_{4-x}$, $Ta(OMe)_5$, $Ta(OEt)_5$, $Ta(OR^1)_4(O-C(R^2)(R^3)-CH_2-OR^4)$, $Ta(OR^1)_4(O-C(R^2)(R^3)-CH_2-N(R^4)(R^5))$, $Ta(NMe_2)_5$, $Ta(NEt_2)_4$, $Ta(NEt_2)_5$, $Ta(=NR^1)(NR^2R^3)_3$, an alkylsilyl chain of the form $SiR^7R^8R^9$ where each $R^i$ is bonded to silicon, a IVA metal source wherein the $M^2$ source is different from the $M^1$ metal source introduced in step b) in the reactor, said IVA metal source being selected from the group consisting of $M^1(OR^1)_4$, $M(NR^1R^2)_4$, and adducts containing these species, a divalent metal A source having the formula $A(-O-C(R^1)-C(R^2)-C(R^3)-O-)(-O-C(R^4)-C(R^5)-C(R^6)-O-)$, and a cyclopentadienyl divalent metal A source having the formula $A(R^1Cp)(R^2Cp)$, wherein each $R^1$ and $R^2$ is independently selected from the group consisting of H and a C1-C6 carbon chain.

* * * * *